US009880149B2

(12) United States Patent
Medintz et al.

(10) Patent No.: US 9,880,149 B2
(45) Date of Patent: Jan. 30, 2018

(54) COATINGS OF SEMICONDUCTOR QUANTUM DOTS FOR IMPROVED VISIBILITY OF ELECTRODES AND PIPETTES

(71) Applicant: Institute of Experimental Medicine of the Hungarian Academy of Sciences, Budapest (HU)

(72) Inventors: Igor L. Medintz, Springfield, VA (US); Bertalan K. Andrasfalvy, Budapest (HU); Kimihiro Susumu, Alexandria, VA (US); James B. Delehanty, Washington, DC (US); Alan L. Huston, Aldie, VA (US); John J. Macklin, Wenonah, NJ (US); Mladen Barbic, Sterling, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 174 days.

(21) Appl. No.: 14/173,652

(22) Filed: Feb. 5, 2014

(65) Prior Publication Data
US 2015/0147803 A1 May 28, 2015

Related U.S. Application Data

(60) Provisional application No. 61/762,419, filed on Feb. 8, 2013.

(51) Int. Cl.
*G01N 33/487* (2006.01)
*C12M 1/42* (2006.01)
(Continued)

(52) U.S. Cl.
CPC ........ *G01N 33/48728* (2013.01); *B01L 3/021* (2013.01); *C03C 17/003* (2013.01);
(Continued)

(58) Field of Classification Search
CPC ... B01L 3/021; B01L 2300/168; C12M 35/02; C03C 17/003; C03C 17/22; C03C 2217/28; G01N 33/48728
See application file for complete search history.

(56) References Cited

U.S. PATENT DOCUMENTS

| 5,989,621 A * | 11/1999 | Lichkus ............... D06B 3/045 427/2.31 |
| 6,501,091 B1 * | 12/2002 | Bawendi ............... B82Y 10/00 257/100 |

(Continued)

OTHER PUBLICATIONS

Ishikawa et al, "Fluorescent pipettes for optically targeted patch-clamp recordings" Neural Networks 23 (2010) 669-672.
(Continued)

*Primary Examiner* — William H. Beisner
*Assistant Examiner* — Danielle B Henkel
(74) *Attorney, Agent, or Firm* — US Naval Research Laboratory; Roy Roberts

(57) ABSTRACT

A glass pipette such as an electrode for electrophysiological recording is coated with quantum dots. This greatly aids the ability to observe the glass pipette, particular in tissue as the quantum dots provide an excellent performance under two-photon illumination used to visualize objects at depths of hundreds of microns.

4 Claims, 8 Drawing Sheets

(51) Int. Cl.
  *B01L 3/02* (2006.01)
  *C03C 17/00* (2006.01)
  *C03C 17/22* (2006.01)

(52) U.S. Cl.
  CPC ............ *C03C 17/009* (2013.01); *C03C 17/22* (2013.01); *C12M 35/02* (2013.01); *B01L 2300/168* (2013.01); *C03C 2217/28* (2013.01)

(56) References Cited

U.S. PATENT DOCUMENTS

| | | | |
|---|---|---|---|
| 8,034,609 B2 | 10/2011 | Hoh et al. | |
| 2004/0076749 A1* | 4/2004 | Lee .................. | G03F 7/162 427/240 |
| 2008/0131909 A1* | 6/2008 | Clark ................. | B82Y 5/00 435/7.1 |
| 2011/0097797 A1 | 4/2011 | Delehanty et al. | |
| 2011/0098445 A1 | 4/2011 | Mattoussi et al. | |
| 2011/0117648 A1 | 5/2011 | Chiou et al. | |
| 2011/0312190 A1* | 12/2011 | Ichino .............. | B05D 1/005 438/782 |

OTHER PUBLICATIONS

Xu NL, Harnett MT, Williams SR, Huber D, O'Connor DH, Svoboda K, Magee JC. "Nonlinear dendritic integration of sensory and motor input during an active sensing task." Nature (2012) 492:247.

Andrasfalvy, BK, Zemelman, BV, Tang, JY, Vaziri, A. "Two-Photon Single-Cell Optogenetic Control of Neuronal Activity by Sculpted Light." Proc. Nat. Acad. Sci. U.S.A. (2010) 107:11981.

Kitamura, K, Judkewitz, B, Kano, M, Denk, W, Häusser, M. "Targeted Patch-Clamp Recordings and Single-Cell Electroporation of Unlabeled Neurons In Vivo." Nature Methods (2008) 5:61.

Jia, H, Rochefort, NL, Chen, X, Konnerth, A. "In Vivo Two-Photon Imaging of Sensory-Evoked Dendritic Calcium Signals in Cortical Neurons." Nature Protocols (2011) 6:28.

Medintz et al. "Quantum dot bioconjugates for imaging, labelling and sensing" Nature Materials. vol. 4, p. 425-446, Jun. 2005.

Hoogland et al. "A solution-processed 1.53 um quantum dot laser with temperature-invariant emission wavelength" Apr. 17, 2006/ vol. 14, No. 8 / Optics Express 3273-3281.

International Search Report for PCT/US2014/014925.

Written Opinion of the International Searching Authority for PCT/US2014/014925.

* cited by examiner

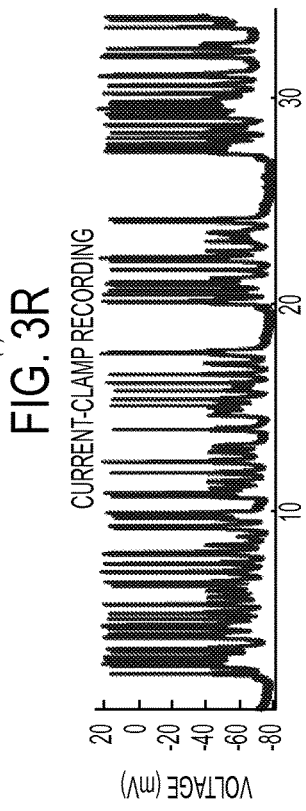
FIG. 3R
FIG. 3S
FIG. 3T
FIG. 3U
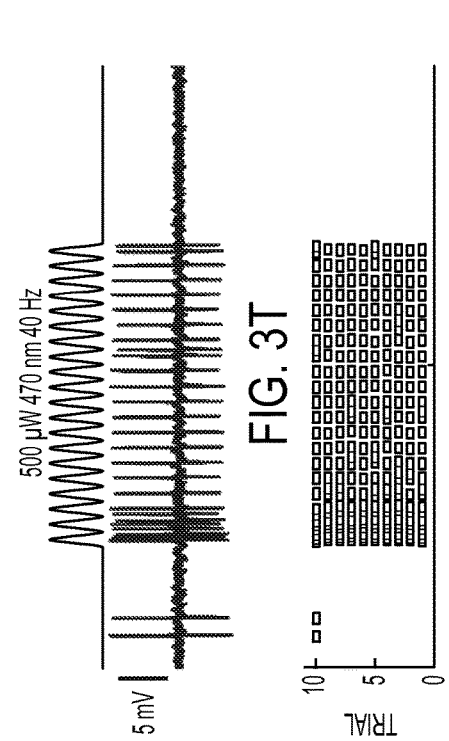
FIG. 3P
FIG. 3Q
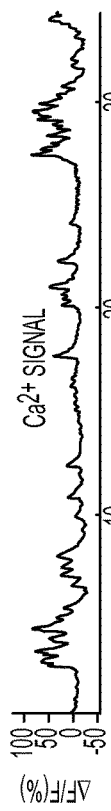
FIG. 3L
FIG. 3M
FIG. 3N
FIG. 3O

COATINGS OF SEMICONDUCTOR QUANTUM DOTS FOR IMPROVED VISIBILITY OF ELECTRODES AND PIPETTES

CROSS-REFERENCE TO RELATED APPLICATIONS

This application claims the benefit of U.S. Provisional Application 61/762,419 filed on Feb. 8, 2013, the entirety of which is incorporated herein by reference.

BACKGROUND

A useful research tool in neurobiology is the use of electrophysiological recording technology to monitor the electrical properties and response of a target cell in neuronal cell culture or brain tissue either in vitro or in vivo. Typically, a glass pipette is shaped to have an extremely fine point (e.g., 1-2 µm) and this is then filled with buffer and electrically connected to a recording device. This recording pipette and the target cells are visualized under a microscope using some type of direct-visible illumination. The pipette is then carefully directed to the target cell and a seal is made between the cellular plasma membrane and the glass pipette (in the case of a patch clamp recording), or the cell is pierced (in the case of whole cell recording with a sharp electrode). In the case of a patch clamp recording, gentle suction ruptures the membrane patch, preserving the seal to get undisturbed connection between the cytosol and the probe interior to isolate the cellular electrical response. Electrophysiological monitoring and recording of the cellular response can then be made over time and in response to environmental or other changes.

Given the extremely small size scale of the cells and pipette tip along with the inherently delicate nature of these biological systems, in many cases it is critical to visibly monitor the tip and targeted patch continuously during these types of experiments and assays. This allows the operator to confirm that the tip-cell seal remains intact, that the tip is correctly positioned, and that the tip and/or cells are viable and uncompromised. During in vitro recordings of brain tissue slices (typically a few 100 µm thick) or in vivo within animals, the recording pipettes/tips have to penetrate in deep tissue (over several 100 µm); here 2-photon laser illumination is typically the best, and sometimes only, technique for producing images from fluorescently labeled cells, probes and processes. Simultaneous fluorescence and visible imaging is generally impossible due to both the depth of the tissue and the nature of the recordings. Until now, the most common method used to make glass pipettes visible under such 2-photon illumination and in the tissue depth needed has been to fill the pipette with fluorescent dyes that are relatively non-toxic to these systems. These include fluorescein or AlexaFluor 594, for example. The operator then blows out or ejects dye during the approach of the tip to the cell. As living cells do not take up the dye, they can be visualized as dark "shadows" against the bright background within a given tissue. But in deeper tissue, the accumulation of such ejected dye makes the visibility poorer and complicates the recognition of cells and patching. The dyes typically used in such formats have small 2-photon action cross sections, which means that a high relative concentration of dye and a relatively high laser power typically have to be used. The dyes often are susceptible to photobleaching in these configurations and the higher laser power dramatically shortens the experimental time available as it can rapidly cause photothermal tissue damage. Additionally, there are many configurations where the addition of dye is not desired such as where cells already express some fluorescent protein-like green fluorescent protein (GFP) tags or genetically encoded calcium indicators (GECI) for $Ca^{2+}$ measurements.

In view of the difficulties associated with implementation of this type of patch clamp technique, there has long been a desire to create an electrophysiological recording pipette that is itself clearly visible under 2-photon microscopic illumination. In particular, a brightly fluorescent pipette that negates the need for ejecting dye to patch labeled cells in deep tissue would be a great advantage for further exploration of in vivo cellular physiology. A need exists for a borosilicate glass pipette visible under 2-photon illumination. Techniques described herein provide the features to accomplish this with few, if any, apparent disadvantages.

BRIEF SUMMARY

As described herein, the above difficulties are overcome by coating a recording pipette with luminescent semiconductor quantum dots (QDs) and then using this pipette to visualize the probe under two-photon microscopic illumination while performing simultaneous electrophysiological recordings and/or other measurements such as calcium monitoring. This new technique encompasses several aspects.

In one embodiment, device comprises a glass pipette of a size suitable for electrophysiological recording, coated with a plurality of quantum dots, thereby causing the quantum dots to coat the glass pipette.

In another embodiment, a method of coating a glass pipette with quantum dots includes providing quantum dots suspended in an organic solvent, and contacting a glass pipette of a size suitable for electrophysiological recording with the quantum dots suspended in an organic solvent. Optionally, the organic solvent contains a dissolved polymer such as polystyrene or poly(methyl methacrylate) (PMMA).

A further embodiment is a kit comprising: quantum dots and an organic solvent suitable for suspending the quantum dots for coating on a glass pipette. Optionally included are printed instructions for coating the glass pipette with the quantum dots. Variations may include a kit having quantum dots provided in a dried form or already suspended in an organic solvent.

BRIEF DESCRIPTION OF THE DRAWINGS

FIG. 1A shows normalized absorption and photoluminescence (PL) spectra of the 530-, 550-, and 625 nm emitting QDs. Molecular extinction coefficients at the wavelengths corresponding to the first exciton peak along with PL quantum yields (QY) are: 530 QD 159,092 $M^{-1}$ $cm^{-1}$ at 501 nm and 19%; 550 QD 120,000 $M^{-1}$ $cm^{-1}$ at 533 nm and 33%; 625 QD 500,000 $M^{-1}$ $cm^{-1}$ at 610 nm and 45%, respectively. FIGS. 1B and 1C show two-photon (2P) fluorescence excitation spectra for the 530-(1 µM) and (c) 625 nm emitting QDs (20 nM) superimposed over that of a fluorescein (1 µM) at pH 11 (FIG. 1B) or Alex Fluor 594 (1 µM) (FIG. 1C) in water used as standards. Spectra were collected and averaged over a forward and back scan through the range of excitation wavelengths. Note the two different intensity scales where QD PL were consistently ≥10× higher than the corresponding standards and necessitated use of far more dilute samples in some cases. Wavelength corresponds to the two-photon (2P) laser excitation wavelength and the 2P cross sections ($\varphi\sigma_2$) in Goeppert-Mayer (GM) units determined for each sample at 790 nm is presented inset. See Supporting Information (SI) for 2P characterization of the 550 QDs.

FIG. 2A shows a 530 QD-coated green pipette used for patching a red fluorescent cholecystokinin-(CCK) positive interneuron from a BAC-CCK-Ds-Red mouse (laser power 15.3 mW). FIG. 2B shows a 550 QD-coated yellow pipette used for patching a native rat hippocampal CA1 pyramidal neuron and loading it with the red dye Alexa Fluor 594 (AF594, laser power 19 mW). FIG. 2C shows 625 QD-coated red pipette used for patching a CA1 pyramidal neuron. Green fibers expressing ChR2-eGFP are projection axons from the basolateral amygdala that was injected and with an adeno-associated viral expression vector (laser power 13.4 mW). FIG. 2D shows 625 QD-coated red pipette with only the tip coated used for patching a GFP-PV positive interneuron from the hippocampus of a GFP-PV-Ds-Red double mouse. Panels from left: I-III, z-stack 2P images obtained in the red channel (I), green channel (II), and merged (III); IV, combined red and green image in a single focal plane at the soma; V, voltage responses to positive and negative current injections (50-250 pA) in the cells shown on the left. FIG. 3A shows a composite Z-stack 2P image of a rat hippocampal CA1 pyramidal neuron loaded with the $Ca^{2+}$ sensor OGB-1 (100 μM, green) through a 625 QD-coated patch pipette (red) in an acute brain slice. Circles indicate dendritic regions used for subsequent $Ca^{2+}$ recording and these are displayed magnified larger on the right with the corresponding numbers (FIGS. 3B, 3C, 3D, and 3F). Increasing number of APs were evoked by 50-160 pA positive current injections (FIG. 3E). $Ca^{2+}$ signals evoked by the backpropagating APs at the dendritic locations are plotted in white at left for each site superimposed over composite fluorescent micrograph. FIG. 3G, shows a Z-stack 2P image of a rat hippocampal CA1 pyramidal neuron loaded with 50 μM Alexa Fluor 594 (red) through a 550 QD-coated patch pipette in an acute slice (same cell shown in FIG. 1e). Dendritic region and 12 spines selected for 2P glutamate uncaging are shown enlarged in the white box inset in FIG. 3G. FIG. 3H shows individual uncaging-evoked excitatory postsynaptic potentials (gluEPSPs) evoked with 200 ms inter-spine intervals (ISI) at the indicated spines. FIG. 3I shows synchronous uncaging at the 12 spines (total inter-spine interval=0.3 ms) evokes a dendritic spike (voltage trace, arrow points to spike), indicated by a corresponding peak on the dV/dt trace. FIG. 3J shows a Z-stack 2P image of a rat hippocampal CA1 pyramidal neuron loaded with 100 μM OGB-1 (green) through a 625 QD-coated patch pipette in an acute slice. Dendritic region and 3 spines selected for 2P glutamate uncaging are shown enlarged in the white box inset of FIG. 3J, along with the imaging line. In FIG. 3K, the top trace presents individual uncaging-evoked gluEPSPs evoked with 200 ms ISI at the indicated spines. Bottom traces show $Ca^{2+}$ signals recorded from the individual spines. FIGS. 3L through 3L show representative sensing with QD-coated probe tips in vivo. FIGS. 3L, 3M, and 3P, respectively, show red, green and merged channel single scan images of a GCamp6 expressing mouse cortical L2/3 pyramidal neuron patched with a 625 QD-coated pipette in vivo. Images were obtained 207 μm deep in the brain. Right GCamp6 $Ca^{2+}$ signals (FIG. 3R) induced by spontaneous spiking activity (FIG. 3S). FIGS. 3O, 3N, and 3Q, respectively, show red, green and merged channel single scan images of a mouse cortical interneuron expressing GFP under the control of the vesicular GABA transporter (VGAT) promoter, patched with a 530 QD-coated pipette in vivo. After recording spiking activity first in cell-attached mode, the cell was loaded with Alexa Fluor 594 by breaking into the whole cell. FIG. 3T shows how a 40 Hz sine wave-modulated 470 nm laser light (delivered through an optical fiber located near the patched cell) evokes firing of the patched neuron (, single trial trace; FIG. 3U shows cumulative results of 10 trials).

DETAILED DESCRIPTION

Definitions

Figure 1A:
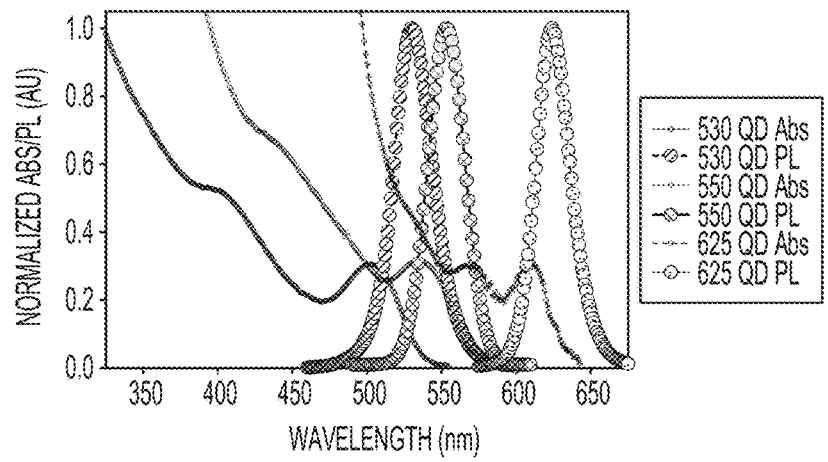
FIGS. 1A through 1C show photophysical properties of the QDs utilized.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

The term "quantum dot" or "QD" as used herein refers to an inorganic semiconductor crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell"

material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

DESCRIPTION

Described herein is a method for using semiconductor nanocrystals termed quantum dots (QDs) to controllably coat portions or the entire inside and/or outside of electrophysiological recording patch clamp probes/pipettes and to provide direct fluorescent or multiphoton fluorescent imaging and visualization in the presence or absence of other fluorescent dyes and conductive buffer during electrophysiological readings of cells in culture, cells in ex vivo neuronal tissues and in vitro slices, and even in neuronal cells in vivo.

The photophysical properties of QDs suggest they may be ideal for the challenge of imaging a pipette for electrophysiological recording. These nanocrystals, defined by the ability to tune their photoluminescence (PL) via core size/composition, display several desirable optical properties including high quantum yields (QY), remarkable resistance to photobleaching/chemical degradation, narrow and symmetrical PL emission (full-width-at-half-maximum ~25-35 nm), broad absorption spectra that increase continuously towards the UV which are also coupled to large one-photon ($\epsilon=10^4$-$10^7$ $M^{-1}$ $cm^{-1}$) and some of the highest high two-photon (2P) absorption cross-sections ($\sigma_{TP4}=10^3$-$10^4$ GM) available. For imaging in tissue, 2P techniques have the advantages of allowing imaging at substantially greater depth compared to other approaches.

Indeed, QD potential for 2P imaging in deep tissue has been repeatedly confirmed. QD-coated pipettes were clearly visible even at depths of 500 µm, while using ~70% less laser power compare to classical approach of pipette visualization using soluble fluorescent dye in the internal solution. Also, the QD-coated pipette shows the brightest fluorescence intensity at the tip, whereas the tip intensity is lowest when using classical approaches. Thus, the QD coating serves well for accurately determining the location of the pipette tip in the tissue, which is critical as this is the active region of the pipette.

Coating with QDs as described has the additional advantage of providing a relatively robust and durable coating. For example, in Ishikawa et al, "Fluorescent pipettes for optically targeted patch-clamp recordings," *Neural Networks* 23 (2010) 669-672, a coating of conventional fluorophore conjugated to albumin was applied to patch-clamp pipettes. However, the results described therein were difficult to replicate, with the fluorophore coating undesirably detaching from the pipette in vivo upon contact with the dura. In contrast, the present technique enjoys the advantage of hydrophobic QDs strongly adhering to glass. This effect may be enhanced when the QD coating is applied using an organic solvent containing a dissolved polymer such as polystyrene or poly(methyl methacrylate) (PMMA), so that the coated QDs are embedded in the polymer. These advantages are compounded with the benefits noted above with regard to QDs and two-photon imaging, so that electrodes and pipettes coated as described herein may be visualized at significantly greater depths than those employing conventional fluorophore.

Potential uses include areas where visualization of probes for recording electrical or chemical signals or delivering materials is beneficial, such as in conjunction with direct or multiphoton microscopic visualization. Also contemplated are coating kits (including some or all of the components required to coat a glass pipette or electrode) or precoated probes. The multicolor emission of different QD samples can allow for choice in emission color or the possibility of multicolor coatings and simultaneous two or more color monitoring of patch clamps.

As described herein, QDs can be utilized for direct probe imaging in brain concurrent with electrophysiological recordings and calcium sensing without compromising inherent electrical signaling/neuronal activity.

The recording pipette is preferably coated with luminescent semiconductor QDs that are surface functionalized with an extremely hydrophobic moiety or "ligand." The strong hydrophobicity means that the QD coat does not leach off or become soluble intracellularly or become soluble in or foul the buffer that is within the pipette tip, nor exhibit "leaky" aspects around the cell exterior. Coating can include just the tip, or an extended portion of the pipette, and include the inside and/or outside area of the pipette or probe as desired. Other methods and chemistries that attach the QDs to the pipette tip in a similar manner may also suffice.

The QD-coated pipette may be used to provide single- or multiphoton imaging and visualization of patched cells located within tissues. This is provided by the QDs photoluminescence (PL) under a 2-photon microscope. This can be in the presence or absence of other fluorescent dyes and/or conductive buffer.

Simultaneous patch clamp electrophysiological recording are possible with the probe, optionally in conjunction with other related measurements such as $Ca^{2+}$ sensing. This includes such types of measurements normally made with such patch clamp systems (e.g. cell firing, depolarization, hyperpolarization, etc.) as the QDs do not compromise the innate ability of the probe's electrical measurements.

Use of differentially coated/colored probe pipettes is also envisioned. For example, multiple pipettes may be coated with different emissive QDs and these can allow simultaneous readings to be collected from two or more neuronal cells, which may be in direct contact with each other.

EXPERIMENTAL

Figure 1B:
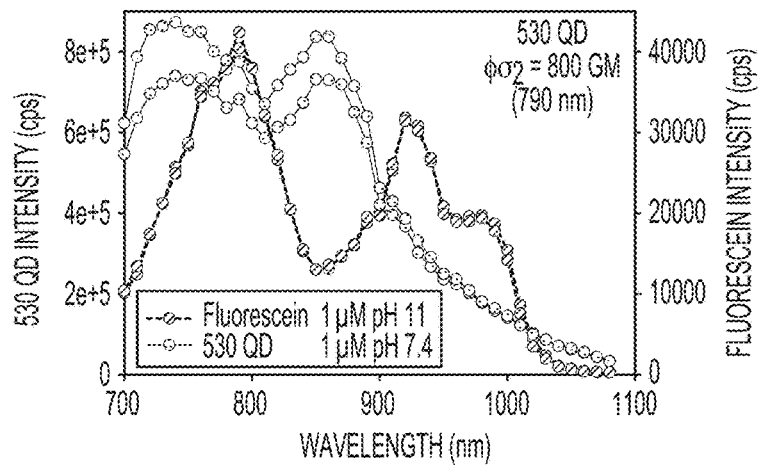
Figure 1C:
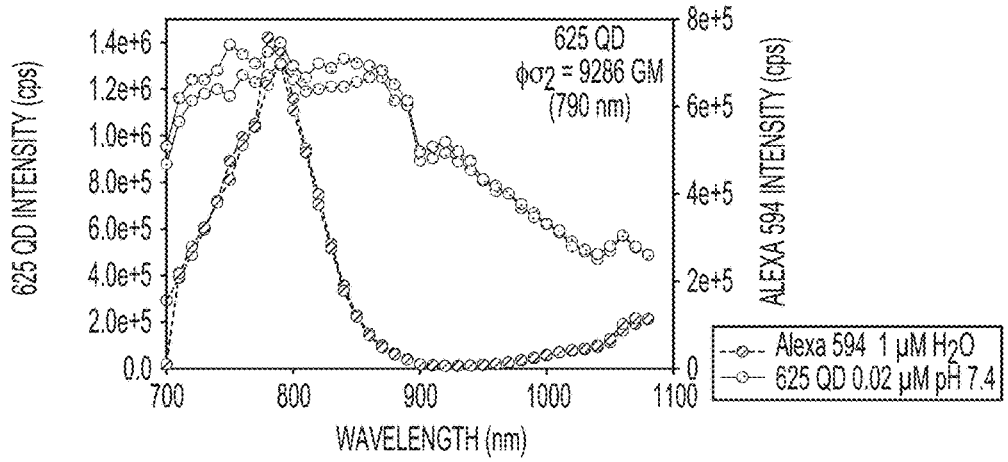

To generate probes suited for contrasting neurons coated by various fluorophores (typically endogenously expressed green or red fluorescent proteins), a series of QDs were used including green 530-, yellow 550- and red 625 nm emitting CdSe/ZnS core/shell materials (FIG. 1A). QDs were used either in toluene or hexane with native phosphine/hexadecylamine coordinating ligands present on the surface for probe coating or cap-exchanged with polyethylene glycol (PEG) modified- or zwitterionic-terminated dihydrolipoic acid ligands (DHLA-PEG and DHLA-CL4, respectively) for characterization. First, the $\varphi\sigma_2$ and 2P fluorescence excitation spectra for the QDs were determined as described in Muetze et al. *Biophys. J* 102, 934-944 (2012). FIGS. 1B and 1C show experimentally measured 2P peak brightness spectra for the 530- and 625 nm QDs in direct comparison to fluorescein and Alexa Fluor 594 dye standards; note the differences in sample concentrations and intensity. $\varphi\sigma_2$ for the 530-, 550- and 625 nm emitting QDs at 790 nm were estimated at 800, 1143 and 9286 GM units, respectively. For comparison, $\varphi\sigma_2$ of fluorescein (38 GM 780 nm, QY-0.9 pH 11), Alexa Fluor 488 (70 GM 790 nm, QY-0.9) and Alexa Fluor 594 (100 GM 790 nm, QY-0.6) are significantly smaller (~20-240× lower). Assuming that a probe could be uniformly coated with an equal amounts of 625 QD or the latter dyes, and using a simplistic extrapolation of $(QY*GM)_{QD}/(QY*GM)_{dye}$ at equal 790 nm 2P excitation, the 625 QD probe is expected be ~60-120 times brighter.

For coating probe tips with QDs, a simplified two-part procedure was developed. 530-, 550-, and 625 nm emitting CdSe/ZnS QDs were synthesized and cap-exchanged with the indicated ligands using procedures that are described in detail in Susumu et al., *J. Am. Chem. Soc.* 133, 9480-9496 (2011) and references therein. Native as-synthesized QDs were washed twice to remove the excess ligands present from synthesis. QD samples in toluene or decane were precipitated by the addition of several mLs of an acetone/methanol 50/50 mixture in a 15 or 50 mL tube. The QDs were then centrifuged to a pellet, and the supernatant decanted and discarded. The pellet was dried under nitrogen and the QDs were again resuspended in hexane or toluene. This was followed by another round of washing and precipitation with the QDs being resuspended the final time in hexane for probe coating.

Freshly pulled 4-12 MΩ borosilicate pipette (Science Products, Gmbh) probe tips were then dipped into the QD solution (1-10 µM in hexane) for coating. The coated tips were removed, the solvent allowed to dry and the tip examined with a hand-held UV light source to confirm coating and to observe the intensity. This was repeated until a desirable QD coating/intensity was reached. Alternative versions of this procedure coated only the exterior of the probe or the very tip itself.

Since the native-capped QDs are insoluble in aqueous buffer, they remain attached to the glass probe providing 2P contrast in the presence of buffer and further dyes.

An exemplary method for preparing QD-coated glass electrodes is as follows:

1. Pull the glass pipette with a puller (such as Sutter model P-97).
2. Dip the tip of the pipette into hexane under positive pressure at the back of the pipette to reduce clogging (pressure may be applied using a syringe).
3. Dry the tip in the air or by using a fire polishing system, typically by a short pulse of a half second under visualization of the tip with low heat, using, e.g., a Narishige MF-900 Microforge.
4. Dip the tip into hexane including suspended QDs under positive pressure at the back of the pipette to reduce clogging (pressure may be applied using a syringe). In embodiments, the QDs can be suspended in another organic solvent.
5. Dry the coated tip for few seconds (still under pressure), then check the tip under visual control using the same Microforge, without using any heat.
6. If the tip is clear (not clogged), then it is ready to use. Repeat coating/drying rounds until the desirable photoluminescence (as visualized under UV light) is reached.

In various embodiments, the initial dipping of the pipette into hexane can be into hexane that includes suspended QDs. In embodiments, the QDs can be suspended in an organic solvent other than hexane.

The technique was reduced to practice in examples wherein either the tip or an extended portion of a glass patch clamp probe/pipette was coated by attaching hydrophobic QDs. The probe was then loaded with electrically conductive buffer and used to patch neuronal cells in an in vitro rat brain hippocampal slice. During tissue penetration and formation of a seal between the probe tip containing buffer and the cellular membrane, the QDs were used to visualize and track the probe tip under multiphoton excitation while being monitored on a multiphoton microscope. The electrophysiological activity and electrical response of the neuron were simultaneously monitored while the tip was being visualized. The QDs allowed for continuous visualization and electromonitoring over extended time periods. Control experiments showed that the presence of QDs does not alter the electrophysiology of the cell or the monitoring of other target analytes in the target cell such as calcium.

In particular, patch-clamp recordings in brain slices using patch pipettes coated with each of the QD colors were successfully performed in situ. QD-coated pipettes created gigaseal contacts using the standard blow-and-seal technique similarly to non-QD coated patch pipettes.

Figure 2A:
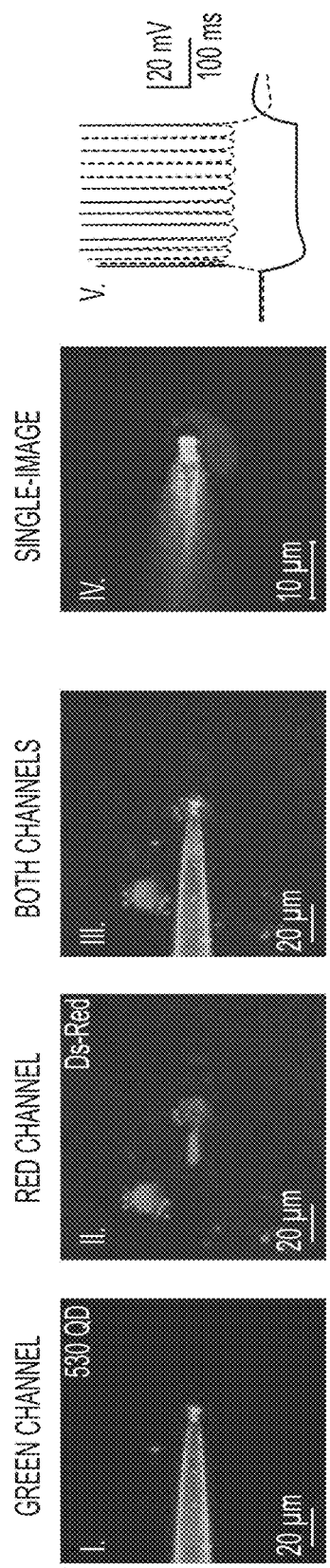
FIGS. 2A through 2D show 2P monitoring of QD-coated pipettes during patching of hippocampal neurons in acute brain slices.
Figure 2B:
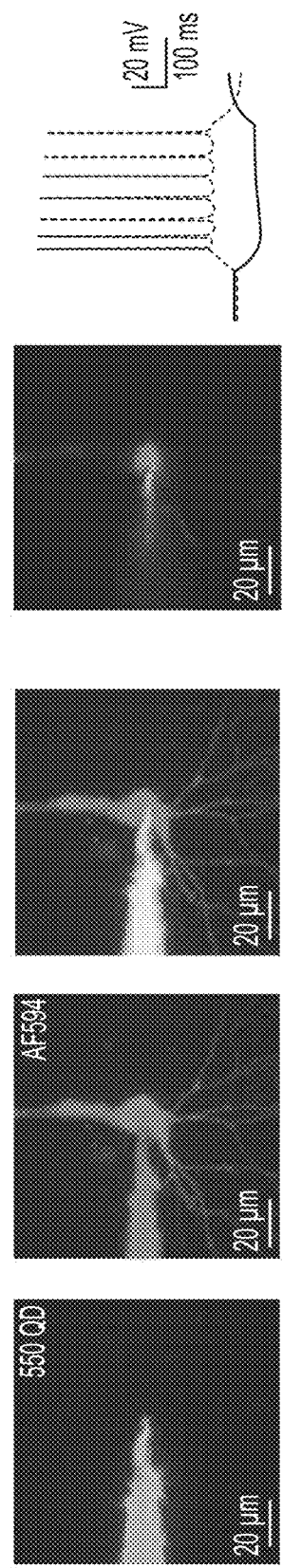
Figure 2C:
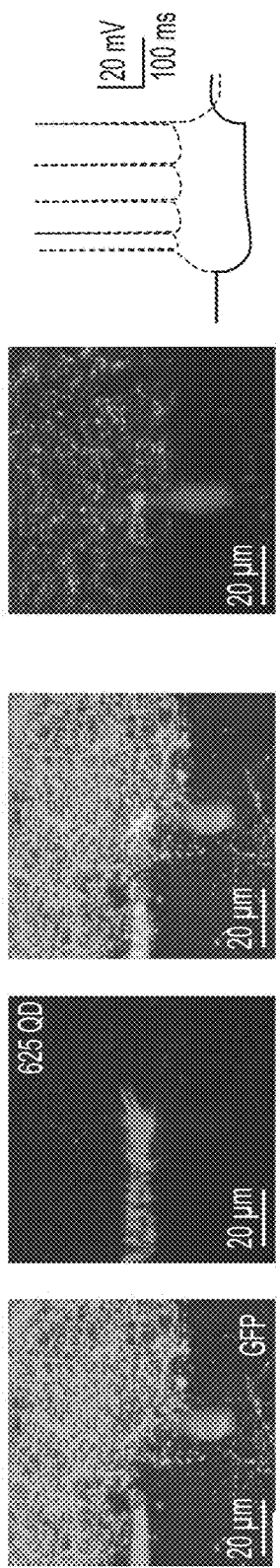
Figure 2D:
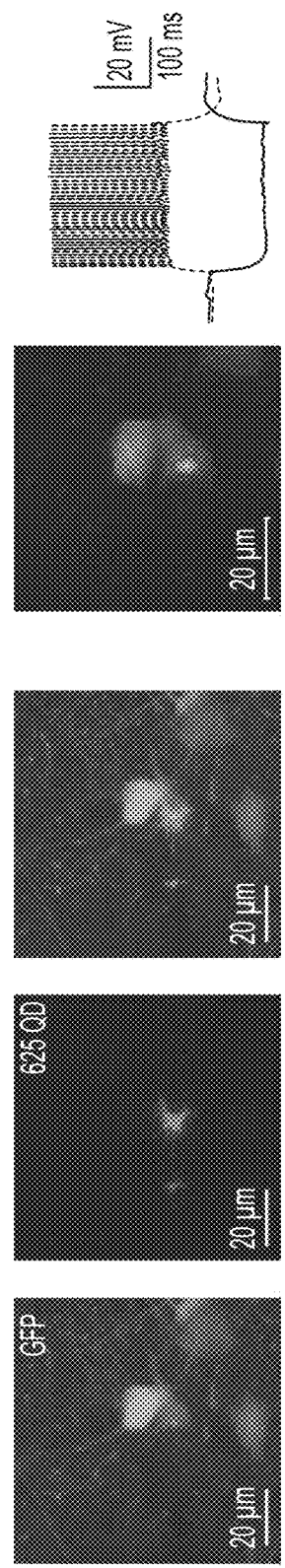
Figure 2E:
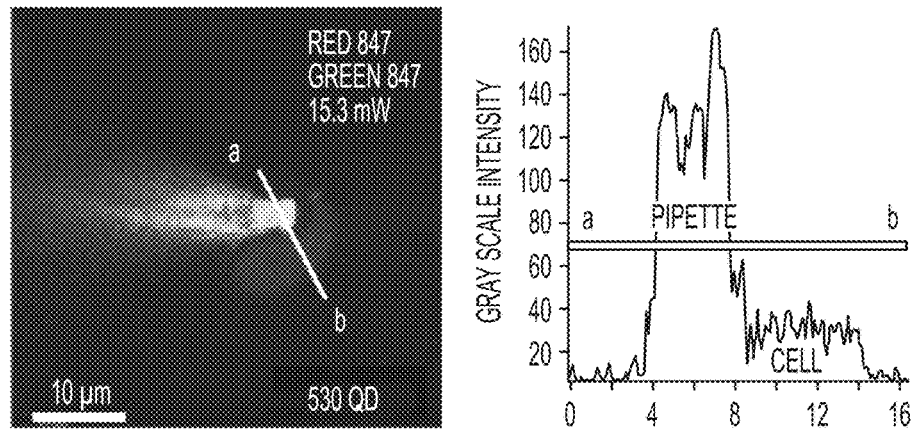
FIG. 2E shows a single scan with merged red/green channels showing a 530 QD-coated tip inserted into a Ds-Red expressing cell along with a plot of the relative gray scale intensities for both colors collected along the line designated by the letters.
Figure 2F:
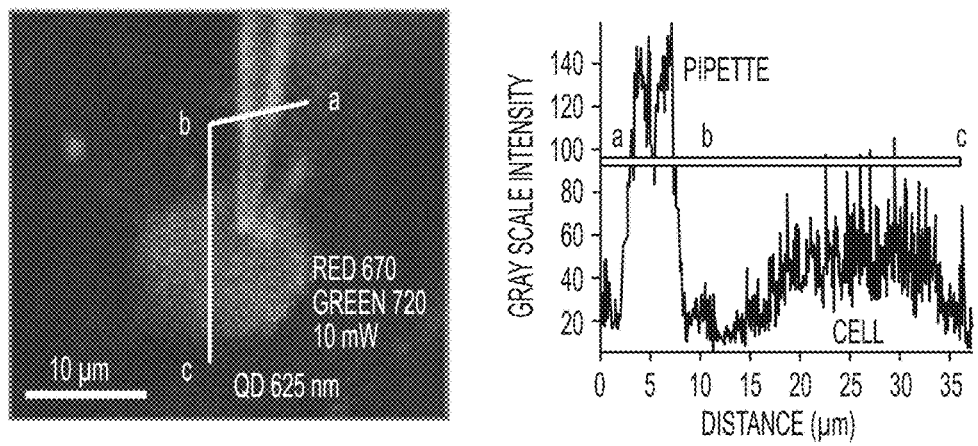
FIG. 2F shows a single scan with merged red/green channels showing a 625 QD-coated tip inserted into a GFP positive cell along with a plot of the relative gray scale intensities for both colors collected along the lines designated by the letters.
Figure 2G:
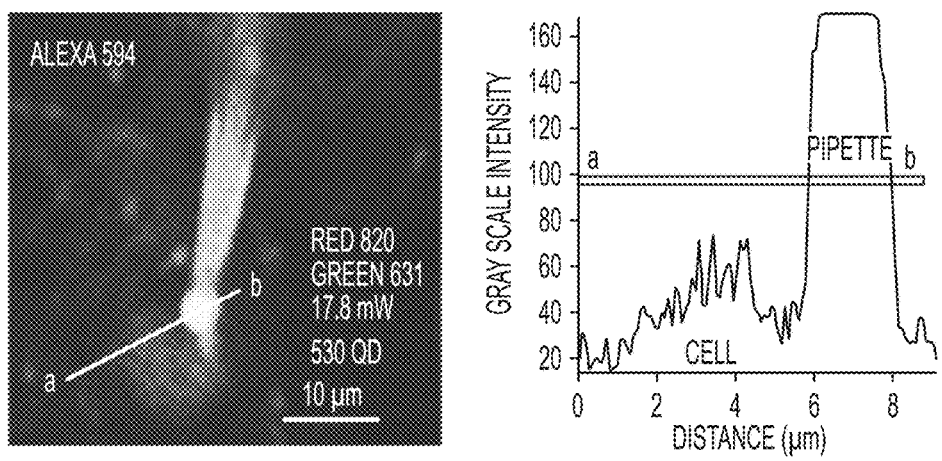
FIG. 2G shows a single scan with merged red/green channels showing a 530 QD-coated tip inserted into a VGAT CHr2 expressing neurons filled with Alexa 594 dye along with a plot of the relative gray scale intensities for both colors collected along the line designated by the letters. Values in FIGS. 2E through 2G are detector gain settings and laser excitation
Figure 3A:
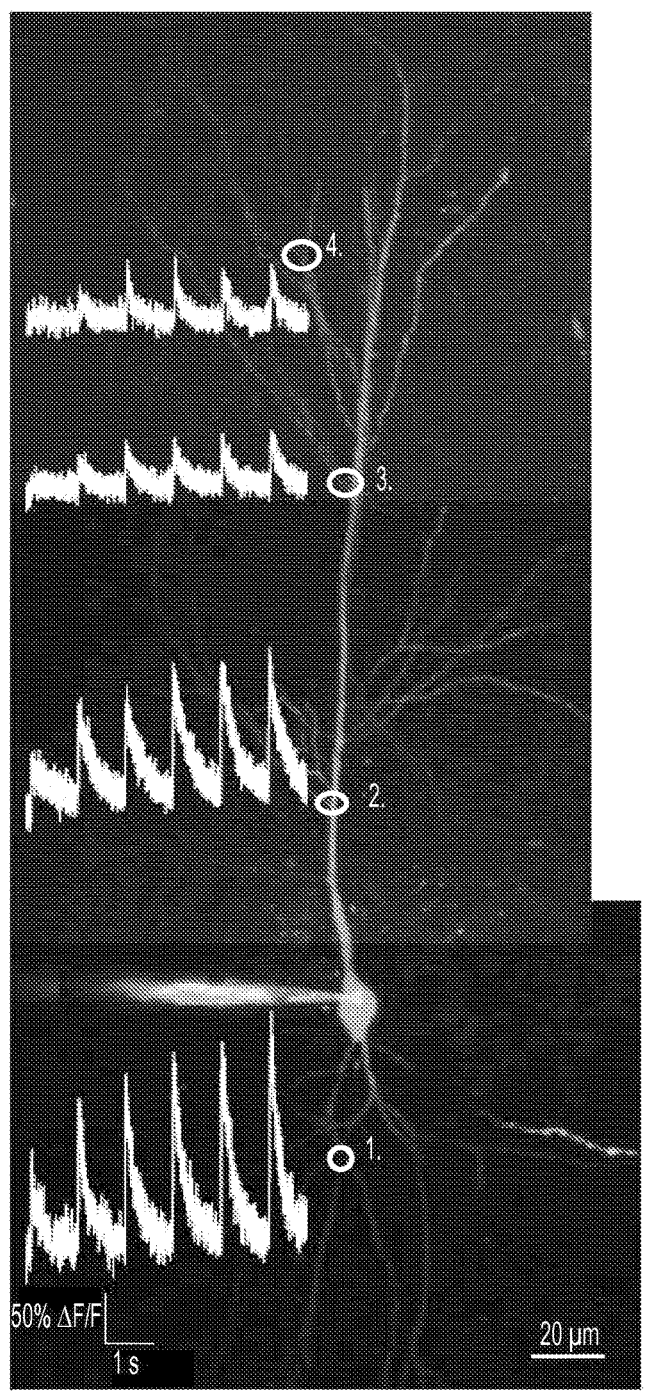
FIGS. 3A through 3K show results of sensing with QD-coated probe tips.
Figure 3B:
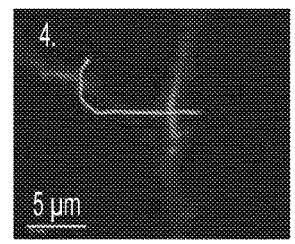
Figure 3C:
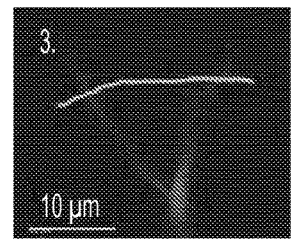
Figure 3D:
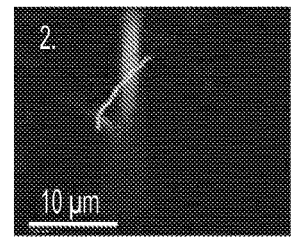
Figure 3E:
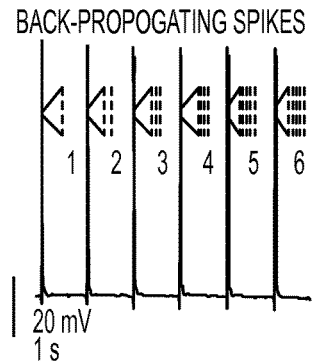
Figure 3F:
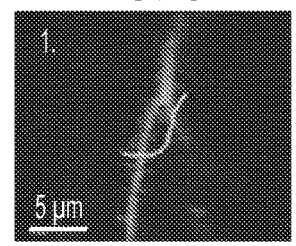
Figure 3G:
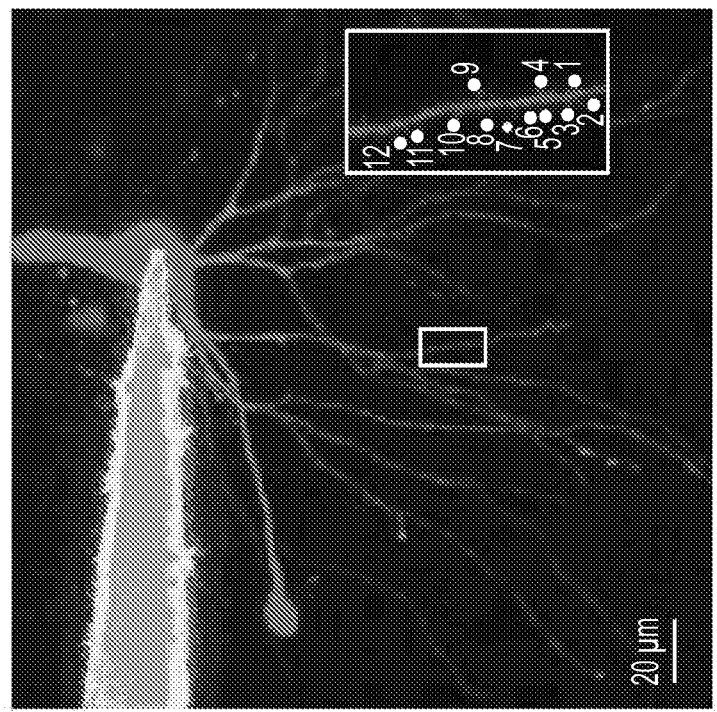
Figure 3H:
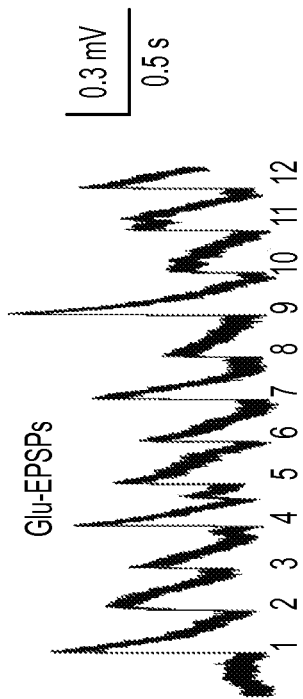
Figure 3I:
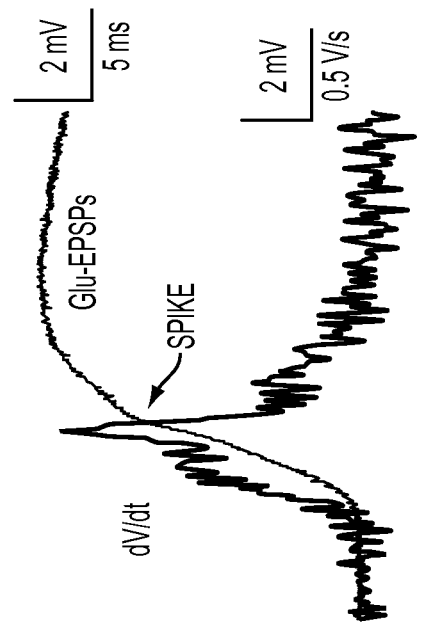
Figures 3J, 3K:
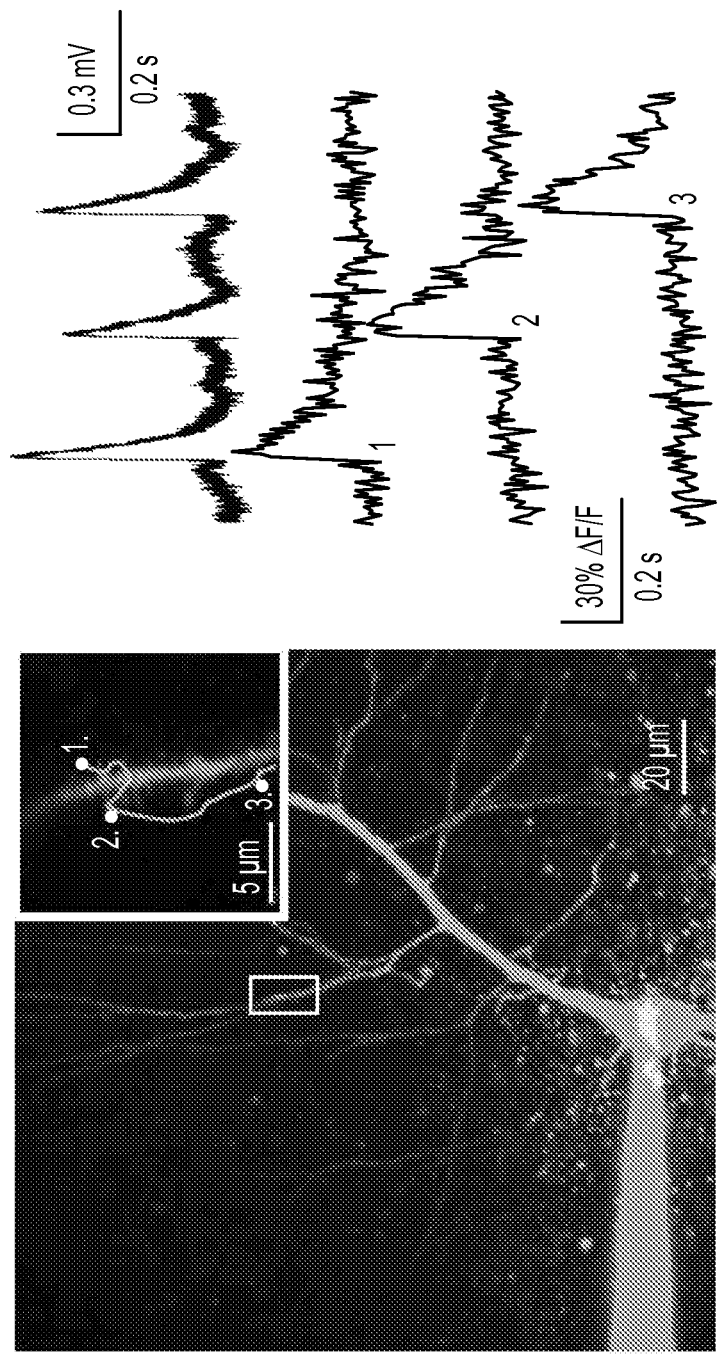

Combinations of QD-coated pipettes and brain slices expressing different fluorescently-labeled cells were used, allowing for contrast with the pipette tips during micrograph collection. Various neuron types were patched including mouse Ds-red-labeled cholecystokinin-(CCK) positive interneurons (FIG. 2A), rat CA1 pyramidal neurons co-loaded with Alexa Fluor 594 (red) dye (FIG. 2B) or expressing channelrhodopsin-2 (ChR2)-eGFP (FIG. 2C), along with a mouse GFP-labeled parvalbumin-(PV) positive interneuron (FIG. 2D). QD-coated pipettes were readily visualized under the 2P microscope up to several hundred microns deep and emitted with intensities that were significantly higher than that of endogenously expressed fluorescent markers (FIGS. 2E through 2G). Indeed, the sensitivity of the photomultiplier detecting QD-pipette signal needed to be scaled down at the excitation laser powers necessary for visualization of the endogenous fluorescent proteins.

The basic electrophysiological properties (somatic firing, voltage responses to a series of positive and negative current injections) of each of the neuron types patched with QD-coated pipettes were normal and indistinguishable from those recorded using non-coated pipettes (FIGS. 2A through 2D, right panels), confirming that the QD-coating did not interfere with electrophysiological recordings. Furthermore, 2P $Ca^{2+}$ imaging from CA1 pyramidal neurons loaded with the $Ca^{2+}$-sensitive dye Oregon Green BAPTA-1 (OGB-1) through the QD-coated pipette revealed normal dendritic and spine $Ca^{2+}$ and voltage signals in response to back-propagating action potentials (FIGS. 3A-3F) as well as to direct synaptic stimulation by 2P glutamate uncaging (FIGS. 3G-3K). To ultimately test any detrimental effect of QDs on cellular properties, injections of DHLA-PEG and DHLA-CL4 QDs were performed directly into the somata of native CA1 pyramidal neurons through regular patch pipettes. Although seal formation was more challenging using this approach, no differences were seen in the basic electrophysiological profile of the neurons, confirming that even the presence of QDs directly in the cellular cytosol did not perturb the underlying electrochemistry.

To demonstrate the qualities of QD-coated pipettes under in vivo conditions, we next used QD-coated patch pipettes to patch cortical L2/3 pyramidal neurons of anaesthetized mice expressing the genetically encoded $Ca^{2+}$ indicator GCamp6 (FIGS. 3L, 3M, 3P, 3R, and 3S). QD-coated pipettes could be clearly visualized in the intact tissue even after probe penetration through the dura. Normal spontaneous electrical activity and corresponding somatic GCamp6 $Ca^{2+}$ signals were observed in the patched cells (FIG. 3S). QD-coated glass pipettes could also be applied to electrophoretically deliver Alexa Fluor 594 dye into individual identified neurons in the brain. Moreover, recordings from Channelrhodopsin2 (ChR2)-expressing VGAT-positive interneurons using QD-coated pipettes verified that activation of ChR2 with 470 nm light produced robust and precisely driven firing as expected (FIGS. 3N, 3O, 3Q, 3T, and 3U).

Together these results demonstrate that QD-coated patch probes can be used to facilitate single cell recordings and labeling even under in vivo conditions. They could be utilized for simultaneous multiphoton imaging and tracking of pipette tips during patch clamp recordings in brain tissue without disrupting the simultaneous electrophysiological neuronal recordings. The QDs provide a number of inherent benefits that facilitate this methodology and that have been unavailable to this point.

Advantages and Applications

The techniques described herein offer a number of advantages. In particular, the use of QD means that high quantum yields and high 2-photon absorption cross-sections are enjoyed. Furthermore, QDs emission wavelengths can be tunable by quantum confinement to be suitable for the desired application, and nanocrystal size and QDs are highly resistant to photobleaching and chemical degradation. Due to their high quantum yield in conjunction with their high 2-photon action cross-sections, the fluorescent signal from QDs is very strong even at sub-mW multiphoton laser power. This allows for visualization of the pipette at lower laser powers, whereas other fluorescent signals from fluorophores like GFP needs at least a few mW to be visible. Moreover, the QD-coated tip does not detrimentally affect seal formation to the target cell within a tissue nor have any detectable adverse physiological consequences. QD surface binding to the recording glass is very strong and stable, even at high laser power, and no alteration could be observed. QD hydrophobicity (while on the pipette), in many cases, appears to makes the cell membrane/pipette seal tighter. The QD presence does not appear to generate a measurable thermo effect. Even at high power 2-photon illumination, the scanning laser beam does not alter the electrophysiological recordings.

Other advantages include the ability to prepare a QD-coated pipette quickly and easily. Such pipettes can be prepared with differentially emissive/colored QDs as desired, and QD-coated pipettes can be prepared and stored for long periods of time without requiring special storage considerations.

QDs could potentially be used to coat and visualize any sort of probes/pipettes, like multi channel extracellular probes, sharp electrodes, viral injection pipettes etc, in a variety of contexts where visualized probe/pipettes would be useful. This would include juxta-cellular and extracellular probes, and other uses including probes for single cell electroporation, enabling treatment of a targeted cell with genetic material, e.g., a plasmid, enabling expression of one or more proteins of interest. In a primary embodiment, such probes and pipettes are glass, however this technique is expected to applicable to probes and pipettes of other materials, particular hydrophobic materials.

Two color QD-based recordings can also be implemented where the pipette is coated and labeled with one color of QD while a second, soluble QD is used to coat and visualize the patch-clamp cell target.

Concluding Remarks

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

REFERENCES

1. Xu N L, Harnett M T, Williams S R, Huber D, O'Connor D H, Svoboda K, Magee J C. "Nonlinear dendritic integration of sensory and motor input during an active sensing task." *Nature* (2012) 492:247.
2. Andrasfalvy, B K, Zemelman, B V, Tang, J Y, Vaziri, A. "Two-Photon Single-Cell Optogenetic Control of Neuronal Activity by Sculpted Light." *Proc. Nat. Acad. Sci. U.S.A.* (2010) 107:11981.
3. Kitamura, K, Judkewitz, B, Denk, W, Hausser, M. "Targeted Patch-Clamp Recordings and Single-Cell Electroporation of Unlabeled Neurons In Vivo." *Nature Methods* (2008) 5:61
4. Jia, H, Rochefort, N L, Chen, X, Konnerth, A. "In Vivo Two-Photon Imaging of Sensory-Evoked Dendritic Calcium Signals in Cortical Neurons." *Nature Protocols* (2011) 6:28

What is claimed is:

1. A method of visualizing comprising:
   providing a glass pipette having a tip and a back;
   contacting the tip with hexane while applying positive pressure to the back; then
   contacting the tip with quantum dots suspended in an organic solvent while applying positive pressure to the back, thereby obtaining a glass pipette with the tip thereof coated with a plurality of quantum dots; then
   confirming that the tip is not clogged; then
   applying the coated tip to a cell culture or tissue,
   visualizing the coated tip under two-photon microscopic illumination sufficient to cause the quantum dots to emit a fluorescent signal while positioning the tip to avoid comprising cells; and
   using the pipette to perform electrophysiological recording.

2. The method of claim 1, wherein said quantum dots are embedded in a polymer.

3. A method of visualizing comprising:
   providing a glass pipette having a tip and a back;
   contacting the tip with hexane while applying positive pressure to the back; then
   contacting the tip with quantum dots suspended in an organic solvent while applying positive pressure to the back, thereby obtaining a glass pipette with the tip thereof coated with a plurality of quantum dots; then
   confirming that the tip is not clogged; then
   applying the coated tip to a cell culture or tissue;
   visualizing the coated tip under two-photon microscopic illumination sufficient to cause the quantum dots to emit a fluorescent signal while positioning the tip to avoid comprising cells; and
   using the pipette to perform calcium sensing.

4. The method of claim 3, wherein said quantum dots are embedded in a polymer.

* * * * *